United States Patent
Brink et al.

(10) Patent No.: US 7,842,673 B2
(45) Date of Patent: Nov. 30, 2010

(54) DELIVERY OF DNA OR RNA VIA GAP JUNCTIONS FROM HOST CELLS TO TARGET CELLS AND A CELL-BASED DELIVERY SYSTEM FOR ANTISENSE OR SIRNA

(75) Inventors: Peter R. Brink, Setauket, NY (US); Michael R Rosen, New York, NY (US); Richard B Robinson, Cresskill, NJ (US); Ira S. Cohen, Stony Brook, NY (US); Arthur Grollman, Setauket, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 346 days.

(21) Appl. No.: 10/583,369

(22) PCT Filed: Dec. 17, 2004

(86) PCT No.: PCT/US2004/042504
§ 371 (c)(1),
(2), (4) Date: May 24, 2007

(87) PCT Pub. No.: WO2005/059111
PCT Pub. Date: Jun. 30, 2005

(65) Prior Publication Data
US 2007/0224176 A1    Sep. 27, 2007

Related U.S. Application Data

(60) Provisional application No. 60/530,555, filed on Dec. 17, 2003.

(51) Int. Cl.
*A01N 43/04* (2006.01)
*A61K 31/70* (2006.01)
*C12Q 1/68* (2006.01)
*C12P 19/34* (2006.01)

(52) U.S. Cl. .................... 514/44; 435/6; 435/91.1; 435/325; 435/375

(58) Field of Classification Search .............. 514/44; 435/6, 91.1, 325, 375; 536/23.1, 24.3, 24.33, 536/24.5
See application file for complete search history.

(56) References Cited

U.S. PATENT DOCUMENTS 5,762,926 A * 6/1998 Gage et al. ............... 424/93.21

OTHER PUBLICATIONS

Braasch et al. (Biochemistry, 2002 vol. 41, pp. 4503-4510).*
Agrawal et al. (Molecular Medicine Today, 2000 vol. 6:72-81).*

(Continued)

*Primary Examiner*—Sean McGarry
*Assistant Examiner*—Terra Cotta Gibbs
(74) *Attorney, Agent, or Firm*—Ditthavong Mori & Steiner, P.C.

(57) ABSTRACT

A method of delivering an oligonucleotide or a plasmid expressing an oligonucleotide into a target cell comprises introducing an oligonucleotide into a donor cell, particularly a stem cell, and contacting the target cell with the donor cell under conditions permitting the donor cell to form a gap junction with the target cell, whereby the oligonucleotide or a product of the oligonucleotide is delivered into the target cell from the donor cell.

20 Claims, 2 Drawing Sheets

OTHER PUBLICATIONS

Gewirtz et al. (Proc. Natl. Acad. Sci., 1996 vol. 93:3161-3163).*
Li et al. (Journal of Cell Biology, 1996 vol. 134:1019-1030).*
Burt et al. (American Journal of Physiology: Cell Physiology, 2001 vol. 280:C500-C508).*
Hammond et al. (Nature Reviews, 2001 vol. 2:110-119).*
Valiunas et al. J. Physiol, 2005 vol. 568.2:459-468. Connexin-specifc cell-to-cell transfer of short interfering RNA by gap junctions.*
Rosenthal et al. (Biochimie, 1995 vol. 77:439-443).*
Salomon et al. (Journal of Investigational Dermatology, 1994 vol. 103(2), Abstract only).*
Hammond et al. (Nature Reviews. Genetics, 2001 vol. 2:110-119).*
Giampuzzi et al. (Jornal of Biological Chemistry, 2001 vol. 276, No. 31:29226-29232).*
Frendo et al., "Involvement of connexin 43 in human trophoblast cell fusion and differentiation, Journal of Cell Science", 2003 vol. 116:3413-3421, see abstract, table 1, p. 3415, first col., and fig. 4.
Peracchia et al., "Is the Voltage Gate of Connexins $CO_2$-sensitivity? Cx45 Channels and inhibition of Calmodulin Expression, Journal of Membrane Biology", 2003 vol. 195:53-62, see abstract, p. 2045, first col., and fig 3.
Li et al., "Inhibiting Gap Junctional Intercellular Communication Alters Expression of Differentiation markers in Osteoblastic Cells", Bone, 1999 vol. 23, pp. 661-666, see fig. 1.
Valiunas et al., "Gap junction channels formed by coexpressed connexin40 and connexin 43", am. J. physiol. Heart Circ. Physiol, 2001 vol. 281; H1675-H1689, see abstract, p. H1677, first col., and table 1, and fig. 6.
Reed et al., "Molecular Cloning and Functional Expression of human Connexin37, and Endothelial Cell Gap junction Protein", Journal of Clinical Investigation, 1993 vol. 91, pp. 997-1004, see abstract and fig. 8.
Elbashir et al., "Duplexes of 21-nucleotide RNAs mediate RNA interference in cultured mammalian cells", Nature, 2001 vol. 411, pp. 494-498, see entire article.
Valiunas, V. et al., "Cardiac Gap Junction Channels Show Quantitative Differences in Selectivity", Circulation Research (2002) vol. 91, pp. 104-111.
Pitts, J. D. et al., "Premeability of Junctions Between Animal Cells. Intercellular Transfer of Nucleotides but Not of Macromolecules" Experimental Cell Research. vol. 104 (1977) pp. 153-163.
Mesnil, M. et al., Bystander Effect in Herpes Simplex Virus-Thymidine Kinase/Ganciclovir Cancer Gene Therapy: role of gap-junctional intercellular communication, Database Medline [Online], Abstract, Cancer Research vol. 60:15 (Aug. 1, 2000) pp. 3989-3999.
Mesnil, M. et al., "Bystander Killing of Cancer Cells by Herpes Simplex Virus Thymidine Kinase Gene is Medicated by Connexins" Database Biosis [Online], Abstract, Proceedings of the National Academy of Sciences of the United States of America, vol. 93:5 (1996) pp. 1831-1835.
Zhu, W. et al., "Increased Genetic Stability of HeLa Cells after Connexin 43 Gene Transfection" Database Biosis [Online], Abstract, Cancer Research, vol. 57:11 (1997) pp. 2148-2150.
Valiunas, V. et al., "Connexin-Specific Cell-to-Cell Transfer of Short Interfering RNA by Gap Junctions", Database Biosis [Online], Abstract, J. of Physiology (Oxford), vol. 568:2, pp. 459-468.
Supplementary European Search Report for EP 04 81 4657 mailed Jun. 22, 2007.

* cited by examiner

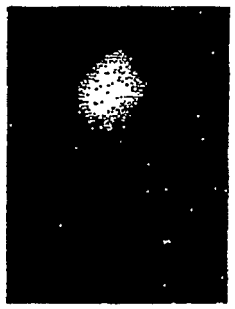
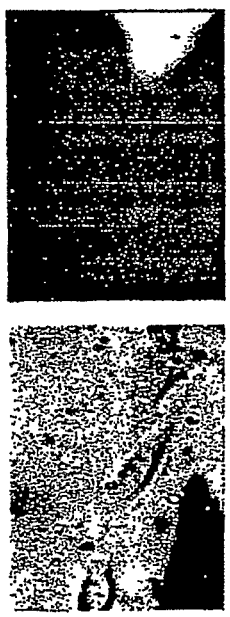
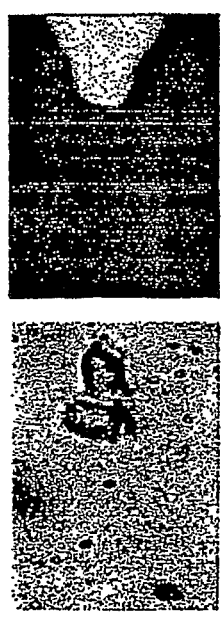
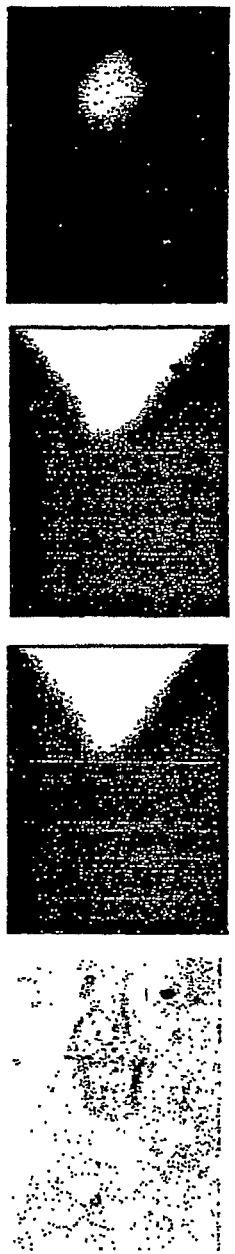
FIGURE 1A 12 mer 5/8/03 - 4
FIGURE 1B 16 mer 5/13/03 - 5
FIGURE 1C 24 mer 6/3/03 - 4
FIGURE 1D 12 mer hybridized 7/22/03 - 3

US 7,842,673 B2

DELIVERY OF DNA OR RNA VIA GAP JUNCTIONS FROM HOST CELLS TO TARGET CELLS AND A CELL-BASED DELIVERY SYSTEM FOR ANTISENSE OR SIRNA

RELATED APPLICATIONS

This is the national phase of PCT Application No. PCT/US2004/042504 filed Dec. 17, 2004, which claims priority to U.S. Application No. 60/530,55 filed on Dec. 17, 2003, the entire contents of which are incorporated herein.

The invention disclosed herein was made at least in part with funding by the U.S. Government, specifically the NHLBI, and NIH(GMS) under grant numbers HL-28958 and GM-55263, respectively, Therefore, the U.S. Government has certain rights in this invention.

BACKGROUND OF THE INVENTION

Throughout this application, various publications are referenced within footnotes or in the text within parentheses. These publications in their entireties are hereby incorporated by reference into this application to more fully describe the state of the art to which this invention pertains. Full bibliographic citations for these references may be found at the end of the specification, preceding the claims.

As described in commonly owned prior application U.S. Ser. No. 10/342,506, filed Jan. 15, 2003, and in publications (1,2) incorporated by reference herein, stem cells have been used to form gap junctions with target tissues. Such stem cells can influence the activity of the target tissues by delivering gene products or small molecules. However, nucleotides in the form of antisense RNA, or DNA, have not been delivered by host cells (such as human mesenchymal stem cells (hMSCs)) to target tissues.

SUMMARY OF THE INVENTION

According to the present invention, RNA can be passed through gap junctions so that engineered cells can be used to deliver RNA to target cells.

According to the present invention, oligonucleotides, either single or double stranded, can be passed, through gap junctions formed by C x 43 in HELA cell pairs, as demonstrated by a single electrode delivery of fluorescent-tagged oligonucleotides to a donor cell and determining their transfer to the target cell via gap junction mediated communication. Accordingly, the invention provides for delivery of oligonucleotides to target cells using any donor cell that forms gap junctions.

According to the invention, a method of delivering an oligonucleotide or a plasmid expressing an oligonucleotide into a target cell is provided, comprising introducing an oligonucleotide into a donor cell, and contacting the target cell with the donor cell under conditions permitting the donor cell to form a gap junction with the target cell, whereby the oligonucleotide or a product of the oligonucleotide is delivered into the target cell from the donor cell.

According to the present invention, a method of delivering an oligonucleotide into a target cell is provided, comprising introducing an oligonucleotide into a human mesenchymal stem cell or other donor cell, and contacting the target cell with the human mesenchymal stem cell or other donor cell under conditions permitting the donor cell to form a gap junction with the target cell, whereby the oligonucleotide or its peptide product is delivered into the target cell from the donor cell.

According to the present invention, a method of delivering an oligonucleotide into a syncytial target cell is provided, comprising introducing an oligonucleotide into a donor cell, and contacting the syncytial target cell with the donor cell under conditions permitting the donor cell to form a gap junction with the syncytial target cell, whereby the oligonucleotide is delivered into the syncytial target cell from the donor cell.

According to the present invention, a method of delivering RNA into a target cell is provided, comprising introducing RNA or a plasmid for RNA into a donor cell, and contacting the target cell with the donor cell under conditions permitting the donor cell to form a gap junction with the target cell, whereby the RNA is delivered into the target cell from the donor cell.

According to the present invention, a method of delivering DNA into a target cell is provided, comprising introducing DNA or a plasmid encoding for DNA into a donor cell, and contacting the target cell with the donor cell under conditions permitting the donor cell to form a gap junction with the target cell, whereby the DNA is delivered into the target cell from the donor cell.

The invention provides a useful treatment in which down regulation of gene activity is desirable (e.g., cancer).

As compared to prior methods wherein delivery of RNA or antisense to target cells is done by a naked plasmid, in the present invention the delivery is via cells, and the transfection rate should be much higher.

DESCRIPTION OF THE DRAWINGS

FIG. 1a shows a 12 member single stranded oligonucleotide passing through gap junction channels composed of connexin 43.

FIG. 1b shows a 16 member single stranded oligonucleotide passing through gap junction channels composed of connexin 43.

FIG. 1c shows a 24 member single stranded oligonucleotide passing through gap junction channels composed of connexin 43.

FIG. 1d shows a 24 member double stranded oligonucleotide passing through gap junction channels composed of connexin 43.

DESCRIPTION OF THE INVENTION

Figure 2:
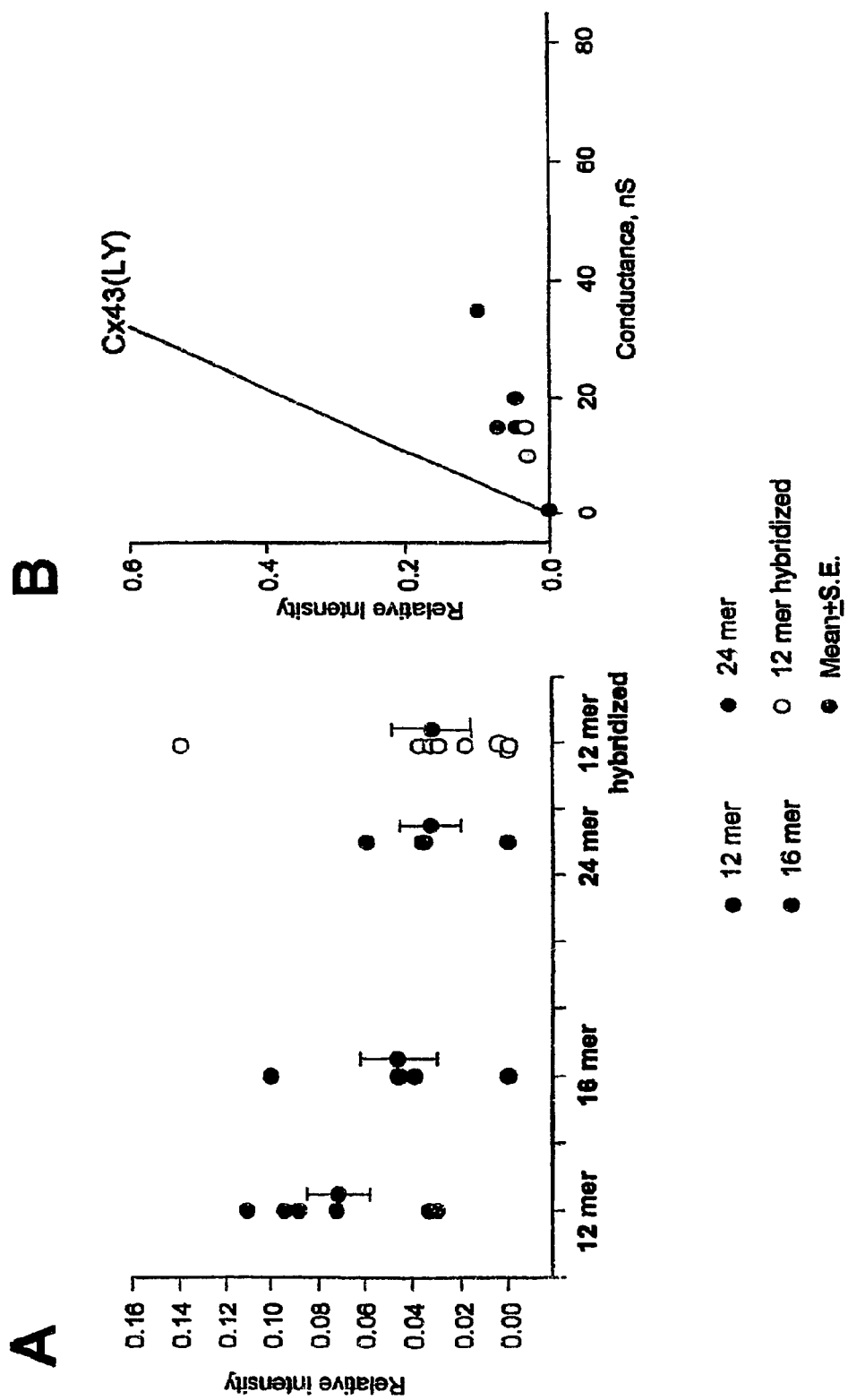
FIG. 2a shows a summary of the data where the x-axis is the length of the oligonucleotide, and the y-axis is the relative intensity of the fluorescent tag in the recipient cell (the cell on the left in all of the examples of FIG. 1) 12 minutes after delivery of the oligonucleotide to the source cell.
FIG. 2b is a graphic representation of junctional conductance on the x-axis versus relative intensity of the fluorescent tag on the y-axis.

According to the invention, a method of delivering an oligonucleotide or a plasmid expressing an oligonucleotide into a target cell is provided, comprising introducing an oligonucleotide into a donor cell, and contacting the target cell with the donor cell under conditions permitting the donor cell to form a gap junction with the target cell, whereby the oligonucleotide or a product of the oligonucleotide is delivered into the target cell from the donor cell.

The oligonucleotide may be RNA that can traverse the gap junction or be transcribed into a peptide that can traverse the gap junction. The oligonucleotide may be DNA. The oligonucleotide may be an antisense oligonucleotide or a cDNA that produces an antisense oligonucleotide that can traverse the gap junction. The oligonucleotide may be a siRNA oligonucleotide or a cDNA that produces a siRNA oligonucleotide that can traverse the gap junction. The oligonucleotide may be a DNA or RNA that produces a peptide that can traverse the gap junction. The plasmid may encode siRNA. The oligonucleotide may comprise 12-24 members. The donor cell may be a human mesenchymal stem cell. The donor cell may be a cell containing or engineered to contain connexin proteins. The target cell may be a cell comprising a syncytial tissue, which may be a cardiac myocyte, a smooth muscle cell, an epithelial cell, a connective tissue cell, or a syncytial cancer cell. The target call may be a white blood cell.

The gap junction channels may be composed of one or more of connexin 43, connexin 40, connexin 45, connexin 32 and connexin 37.

According to the present invention, a method of delivering an oligonucleotide into a target cell is provided, comprising introducing an oligonucleotide into a human mesenchymal stem cell or other donor cell, and contacting the target cell with the human mesenchymal stem cell or other donor cell under conditions permitting the donor cell to form a gap junction with the target cell, whereby the oligonucleotide or its peptide product is delivered into the target cell from the donor cell.

According to the present invention, a method of delivering an oligonucleotide into a syncytial target cell is provided, comprising introducing an oligonucleotide into a donor cell, and contacting the syncytial target cell with the donor cell under conditions permitting the donor cell to form a gap junction with the syncytial target cell, whereby the oligonucleotide is delivered into the syncytial target cell from the donor cell.

According to the present invention, a method of delivering RNA into a target cell is provided, comprising introducing RNA or a plasmid for RNA into a donor cell, and contacting the target cell with the donor cell under conditions permitting the donor cell to form a gap junction with the target cell, whereby the RNA is delivered into the target cell from the donor cell.

According to the present invention, a method of delivering DNA into a target cell is provided, comprising introducing DNA or a plasmid encoding for DNA into a donor cell, and contacting the target cell with the donor cell under conditions permitting the donor cell to form a gap junction with the target cell, whereby the DNA is delivered into the target cell from the donor cell.

The present invention provides a way to pass oligonucleotides (DNA and/or RNA fragments) through gap junction channels. This has been demonstrated in experiments where gap junction channels composed of connexin43 (Cx43) were used in a HeLa cell line.

The experiments determined that oligocomplexes such as DNA or RNA sequences of defined length are able to pass through a gap junction channel. DNA or RNA, forms alpha helixes in solution with minor diameters of 0.9-1.0 nm. Oligonucleotides in the 12-24 member size range are of particular interest. Unique sequences of DNA which could not be broken down into smaller fragments were tagged with a fluorescent probe from Morpholino, a company which specializes in the manufacture of oligo sequences.

The experiments were conducted with a 12 member oligonucleotide, a 16 member oligonucleotide and a 24 member oligonucleotide. The results demonstrated that all three single stranded forms pass through gap junction channels composed of Cx43 (FIGS. 1a, b, and c). Further, two 12 member compliments were hybridized producing a double stranded form and its passage was measured (FIG. 1d). The double stranded version has only a small increase in its minor diameter.

FIG. 2A shows a summary of the data where the X-axis is the length of the oligonucleotide. The hybridized 12 member oligonucleotide is plotted out of sequence on the X-axis. The Y-axis is the relative intensity of the fluorescent tag in the recipient cell (the cell on the left in all of the examples of FIG. 1) 12 minutes after delivery of the oligonucleotide to the source cell. For each oligonucleotide the individual experimentally derived values are shown along with the mean and standard deviation for each oligonucleotide. In a number of experiments junctional conductance and the transfer of fluorescently labeled oligonucleotide were monitored simultaneously.

FIG. 2B is a graphic representation of junctional conductance on the X-axis versus relative intensity of the fluorescent tag on the Y-axis. For comparison the conductance-intensity relationship for Lucifer Yellow passage through Cx43 gap junction channels is shown (Valiunas et al., 2002)(2). In all cases the relative intensity, which represents the transfer rate from one cell to another, is 5-10 times less than the Lucifer Yellow fluorescence intensity in recipient cells. This lower transfer rate is consistent with the rod-like dimensions of the oligonucleotide, whose minor diameter is 1.0 nm, being less mobile in solution than Lucifer Yellow.

These observations demonstrate that gap junction channels are a feasible delivery port for molecules such as silencing RNA (siRNA) or any other molecule of similar dimension.

We have previously demonstrated that hMSCs make gap junctions with each other and target cells. We have also demonstrated previously that one can load plasmids into stem cells by electroporation. The present results demonstrate that any donor cell type which forms gap junctions with another target cell type (this includes hMSCs as potential donor or target cells) can be used as a vehicle to deliver RNA or DNA.

REFERENCES

1. Plotnikov A N, Shlapakova I N, Danilo P Jr, Herron A, Potapova I, Lu Z, Valiunas V, Doronin S, Brink P R, Robinson R B, Cohen I S, Rosen M R: Human mesenchymal stem cells transfected with HCN2 as a gene delivery system to induce pacemaker function in canine heart. Circulation 108: IV-547, 2003.
2. Valiunas et al., 2002 Cardiac gap junction channels show quantitative differences in selectivity. Cir. Res. 91:104-111

We claim:

1. A method of delivering an oligonucleotide into a target cell comprising: a) introducing the oligonucleotide or a plasmid expressing the oligonucleotide into a donor cell in vitro; and b) contacting the target cell with the donor cell under conditions permitting the donor cell to form a gap junction channel composed of connexin 43 with the target cell, whereby the oligonucleotide is delivered into the target cell from the donor cell by traversing the gap junction and wherein the oligonucleotide is 12-24 nucleotides in length.

2. The method of claim 1, wherein the oligonucleotide is RNA that can traverse the gap junction.

3. The method of claim 1, wherein the oligonucleotide is DNA.

4. The method of claim 1, wherein the oligonucleotide is an antisense oligonucleotide.

5. The method of claim 1, wherein the oligonucleotide is a siRNA.

6. The method of claim 1, wherein the plasmid encodes siRNA.

7. The method of claim 1, wherein the oligonucleotide is 18-22 nucleotides in length.

8. The method of claim 1, wherein the donor cell is a human mesenchymal stem cell.

9. The method of claim 1, wherein the donor cell is a cell engineered to contain connexin 43.

10. The method of claim 1, wherein the target cell is present in a syncytial tissue.

11. The method of claim 10, wherein the cell in the syncytial tissue is selected from the group consisting of a cardiac myocyte, a smooth muscle cell, an epithelial cell, a connective tissue cell, and a syncytial cancer cell.

12. The method of claim 1, wherein the target cell is a white blood cell.

13. A method of delivering an oligonucleotide into a target cell comprising: a) introducing the oligonucleotide into a human mesenchymal stem cell or other donor cell in vitro; and b) contacting the target cell with the human mesenchymal stem cell or other donor cell under conditions permitting the donor cell to form a gap junction channel composed of connexin 43 with the target cell, whereby the oligonucleotide is delivered into the target cell from the donor cell by traversing the gap junction and wherein the oligonucleotide is 12-24 nucleotides in length.

14. A method of delivering an oligonucleotide into a syncytial target cell comprising: a) introducing the oligonucleotide into a donor cell in vitro; and b) contacting the syncytial target cell with the donor cell under conditions permitting the donor cell to form a gap junction channel with the syncytial target cell, whereby the oligonucleotide is delivered into the syncytial target cell from the donor cell by traversing the gap junction wherein the gap junction is composed of connexin 43 and wherein the oligonucleotide is 12-24 nucleotides in length.

15. A method of delivering RNA into a target cell comprising: a) introducing RNA or a plasmid transcribable into RNA into a donor cell in vitro; and b) contacting the target cell with the donor cell under conditions permitting the donor cell to form a gap junction channel composed of connexin 43 with the target cell, whereby the RNA is delivered into the target cell from the donor cell by traversing the gap junction and wherein the RNA is 12-24 nucleotides in length.

16. A method of delivering DNA into a target cell comprising: a) introducing a DNA or a plasmid coding for the DNA into a donor cell in vitro; and b) contacting the target cell with the donor cell under conditions permitting the donor cell to form a gap junction channel composed of connexin 43 with the target cell, whereby the DNA is delivered into the target cell from the donor cell by traversing the gap junction and wherein the DNA is 12-24 nucleotides in length.

17. The method of claim 13, wherein the donor cell is a human mesenchymal stem cell.

18. The method of claim 14, wherein the donor cell is a human mesenchymal stem cell.

19. The method of claim 15, wherein the donor cell is a human mesenchymal stem cell.

20. The method of claim 16, wherein the donor cell is a human mesenchymal stem cell.

\* \* \* \* \*